(12) United States Patent
Mills et al.

(10) Patent No.: US 7,645,056 B1
(45) Date of Patent: Jan. 12, 2010

(54) OPTICAL IRRADIATION DEVICE HAVING LED AND HEAT PIPE

(75) Inventors: Robin Walter Mills, Wiltshire (GB); Klaus Dieter Jandt, Bristol (GB)

(73) Assignee: Koninklijke Philips Electronics N V, Eindhoven (NL)

( * ) Notice: Subject to any disclaimer, the term of this patent is extended or adjusted under 35 U.S.C. 154(b) by 0 days.

(21) Appl. No.: 09/509,433

(22) PCT Filed: Sep. 25, 1998

(86) PCT No.: PCT/GB98/02905

§ 371 (c)(1),
(2), (4) Date: May 30, 2000

(87) PCT Pub. No.: WO99/16136

PCT Pub. Date: Apr. 1, 1999

(30) Foreign Application Priority Data

Sep. 25, 1997 (GB) .................................. 9720443.2
Mar. 20, 1998 (GB) .................................. 9806046.0

(51) Int. Cl.
*F21V 29/00* (2006.01)
*F28D 15/02* (2006.01)

(52) U.S. Cl. ........................ 362/294; 362/373; 362/218; 362/580; 362/249.02; 165/104.21; 165/104.19

(58) Field of Classification Search .................... 362/80, 362/551, 554–556, 572, 573, 580, 218, 294, 362/373, 249.02, 249.11; 385/100, 116, 385/117, 146; 165/104.19, 104.21
See application file for complete search history.

(56) References Cited

U.S. PATENT DOCUMENTS

| 398,383 | A | | 2/1889 | Crommer |
| 3,327,712 | A | * | 6/1967 | Kaufman et al. .............. 606/40 |
| 3,512,027 | A | | 5/1970 | Kupsky |
| 3,548,930 | A | * | 12/1970 | Byrd ...................... 165/104.26 |
| 3,603,382 | A | * | 9/1971 | Paine et al. ............ 165/104.26 |
| 3,638,013 | A | | 1/1972 | Keller |
| 3,677,329 | A | * | 7/1972 | Kirkpatrick ............ 165/104.26 |
| 3,681,592 | A | * | 8/1972 | Hugelshofer ................ 362/580 |
| 3,712,984 | A | | 1/1973 | Lienhard |
| 3,714,981 | A | * | 2/1973 | Noren ......................... 165/47 |
| 3,733,481 | A | | 5/1973 | Kuyt |
| 3,811,493 | A | * | 5/1974 | Bilinski et al. .............. 165/272 |

(Continued)

FOREIGN PATENT DOCUMENTS

CA  2 190 225  6/1997

(Continued)

OTHER PUBLICATIONS

LumiLeds Lighting LLC, *Lumen Maintenance of White Luxeon™ Power Light Sources*, Application Brief AB07, LumiLeds Lighting, US LLC.

(Continued)

*Primary Examiner*—Ismael Negron
(74) *Attorney, Agent, or Firm*—Lando & Anastasi, LLP (57) ABSTRACT

An optical irradiation device incorporating a plurality of LEDs arranged in one or more clusters or arrays. A heat pipe is provided to conduct heat away from the LEDs allowing the LEDs to be driven to produce more radiation than would be possible without the heat pipe.

16 Claims, 4 Drawing Sheets

U.S. PATENT DOCUMENTS

| | | | |
|---|---|---|---|
| 3,868,513 A | 2/1975 | Gonser | |
| 3,872,463 A | 3/1975 | Lapeyre | |
| 3,952,798 A * | 4/1976 | Jacobson et al. | 165/104.26 |
| 3,970,856 A | 7/1976 | Mahaffey et al. | |
| 4,048,490 A | 9/1977 | Troue | |
| 4,114,274 A | 9/1978 | Jones | |
| 4,114,946 A | 9/1978 | Hoffmeister et al. | |
| 4,149,086 A | 4/1979 | Nath | |
| 4,184,196 A | 1/1980 | Moret et al. | |
| 4,185,891 A | 1/1980 | Kaestner | |
| 4,186,748 A | 2/1980 | Schlager | |
| 4,209,907 A | 7/1980 | Tsukada et al. | |
| 4,229,658 A | 10/1980 | Gonser | |
| 4,230,453 A | 10/1980 | Reimers | |
| 4,233,649 A | 11/1980 | Scheer et al. | |
| 4,280,273 A | 7/1981 | Vincent | |
| 4,298,806 A | 11/1981 | Herold | |
| 4,337,759 A | 7/1982 | Popovich et al. | |
| 4,346,329 A | 8/1982 | Schmidt | |
| 4,385,344 A * | 5/1983 | Gonser | 362/573 |
| 4,391,588 A | 7/1983 | Matsui | |
| 4,398,885 A | 8/1983 | Logé et al. | |
| 4,412,134 A | 10/1983 | Herold et al. | |
| 4,445,858 A | 5/1984 | Johnson | |
| 4,450,139 A | 5/1984 | Bussiere et al. | |
| 4,610,630 A | 9/1986 | Betush | |
| 4,666,406 A | 5/1987 | Kanca, III | |
| 4,671,349 A * | 6/1987 | Wolk | 165/47 |
| 4,673,353 A | 6/1987 | Nevin | |
| 4,675,785 A | 6/1987 | Young | |
| 4,716,296 A | 12/1987 | Bussière et al. | |
| 4,729,076 A * | 3/1988 | Masami et al. | 362/294 |
| 4,742,432 A | 5/1988 | Thillays et al. | |
| 4,757,381 A | 7/1988 | Cooper et al. | |
| 4,791,634 A | 12/1988 | Miyake | |
| 4,792,692 A | 12/1988 | Herold et al. | |
| 4,810,194 A | 3/1989 | Snedden | |
| 4,822,335 A | 4/1989 | Kawai et al. | |
| 4,826,431 A | 5/1989 | Fujimura et al. | |
| 4,836,782 A | 6/1989 | Gonser | |
| 4,839,566 A | 6/1989 | Herold et al. | |
| 4,845,405 A | 7/1989 | Yamane et al. | |
| 4,846,546 A | 7/1989 | Cuda | |
| 4,857,801 A | 8/1989 | Farrell | |
| 4,888,489 A | 12/1989 | Bryan | |
| 4,893,354 A | 1/1990 | Janzen et al. | |
| 4,901,324 A | 2/1990 | Martin | |
| 4,935,665 A | 6/1990 | Murata | |
| 4,936,808 A | 6/1990 | Lee | |
| 4,948,215 A | 8/1990 | Friedman | |
| 4,963,798 A | 10/1990 | McDermott | |
| 4,999,310 A | 3/1991 | Kim | |
| 5,003,434 A | 3/1991 | Gonser et al. | |
| 5,007,837 A | 4/1991 | Werly | |
| 5,017,140 A | 5/1991 | Ascher | |
| 5,029,335 A * | 7/1991 | Fisher et al. | 372/36 |
| 5,029,957 A | 7/1991 | Hood | |
| 5,046,840 A | 9/1991 | Abbiss et al. | |
| 5,070,258 A | 12/1991 | Izumi et al. | |
| 5,099,399 A * | 3/1992 | Miller et al. | 362/580 |
| 5,115,761 A | 5/1992 | Hood | |
| 5,147,204 A | 9/1992 | Patten et al. | |
| 5,150,016 A | 9/1992 | Sawase et al. | |
| 5,160,200 A | 11/1992 | Cheselske | |
| 5,161,879 A | 11/1992 | McDermott | |
| 5,162,696 A | 11/1992 | Goodrich | |
| 5,169,632 A | 12/1992 | Duell et al. | |
| 5,173,810 A | 12/1992 | Yamakawa | |
| 5,195,102 A | 3/1993 | McLean et al. | |
| 5,198,678 A | 3/1993 | Oppawsky | |
| 5,201,655 A | 4/1993 | Friedman | |
| 5,233,283 A | 8/1993 | Kennedy | |
| 5,242,602 A | 9/1993 | Richardson et al. | |
| 5,253,260 A | 10/1993 | Palombo | |
| 5,265,792 A | 11/1993 | Harrah et al. | |
| 5,268,812 A | 12/1993 | Conte | |
| 5,278,629 A | 1/1994 | Schlager et al. | |
| 5,283,425 A | 2/1994 | Imamura | |
| 5,290,169 A | 3/1994 | Friedman et al. | |
| 5,302,124 A | 4/1994 | Lansing et al. | |
| 5,309,457 A | 5/1994 | Minch | |
| 5,312,249 A | 5/1994 | Kennedy | |
| 5,316,473 A | 5/1994 | Hare | |
| 5,328,368 A | 7/1994 | Lansing et al. | |
| 5,371,753 A | 12/1994 | Adsett | |
| 5,371,826 A | 12/1994 | Friedman | |
| 5,373,114 A | 12/1994 | Kondo et al. | |
| 5,387,800 A | 2/1995 | Kurtich et al. | |
| 5,418,384 A | 5/1995 | Yamana et al. | |
| 5,420,768 A * | 5/1995 | Kennedy | 362/119 |
| 5,445,608 A | 8/1995 | Chen et al. | |
| 5,457,611 A | 10/1995 | Verderber | |
| 5,471,129 A | 11/1995 | Mann | |
| 5,474,449 A | 12/1995 | Loge et al. | |
| 5,487,662 A | 1/1996 | Kipke et al. | |
| 5,504,764 A | 4/1996 | Pohlmann et al. | |
| 5,521,392 A | 5/1996 | Kennedy et al. | |
| 5,522,225 A | 6/1996 | Eskandari | |
| 5,530,632 A | 6/1996 | Shikano et al. | |
| 5,535,230 A | 7/1996 | Abe | |
| 5,554,855 A | 9/1996 | Ueno | |
| 5,616,141 A | 4/1997 | Cipolla | |
| 5,617,492 A | 4/1997 | Beach et al. | |
| 5,631,987 A | 5/1997 | Lasky et al. | |
| 5,634,711 A | 6/1997 | Kennedy et al. | |
| 5,660,461 A | 8/1997 | Ignatius et al. | |
| 5,664,042 A | 9/1997 | Kennedy | |
| 5,664,864 A * | 9/1997 | Kuth | 362/551 |
| 5,698,866 A | 12/1997 | Doiron et al. | |
| 5,707,139 A | 1/1998 | Haitz | |
| 5,711,665 A | 1/1998 | Adam et al. | |
| 5,729,561 A | 3/1998 | Hironaka | |
| 5,747,363 A | 5/1998 | Wei et al. | |
| 5,759,032 A | 6/1998 | Bartel | |
| 5,762,867 A | 6/1998 | D'Silva | |
| 5,800,478 A | 9/1998 | Chen et al. | |
| 5,803,729 A | 9/1998 | Tsimerman | |
| 5,857,767 A | 1/1999 | Hochstein | |
| 5,873,645 A * | 2/1999 | Belfer | 362/551 |
| 5,912,470 A | 6/1999 | Eibofner et al. | |
| 5,928,220 A | 7/1999 | Shimoji | |
| 5,949,805 A | 9/1999 | Mordaunt et al. | |
| 5,967,653 A * | 10/1999 | Miller et al. | 362/580 |
| 5,975,895 A | 11/1999 | Sullivan | |
| 6,008,264 A | 12/1999 | Ostler et al. | |
| 6,033,223 A | 3/2000 | Narusawa et al. | |
| 6,045,240 A | 4/2000 | Hochstein | |
| 6,046,460 A | 4/2000 | Mertins | |
| 6,065,965 A | 5/2000 | Rechmann | |
| 6,068,474 A | 5/2000 | Senn et al. | |
| 6,077,073 A | 6/2000 | Jacob | |
| 6,102,696 A | 8/2000 | Osterwalder et al. | |
| 6,113,212 A | 9/2000 | Ng | |
| 6,159,005 A | 12/2000 | Herold et al. | |
| 6,161,937 A | 12/2000 | Rosenstatter | |
| 6,200,134 B1 | 3/2001 | Kovac et al. | |
| 6,208,788 B1 | 3/2001 | Nosov | |
| 6,402,347 B1 * | 6/2002 | Maas et al. | 362/294 |
| 6,969,180 B2 * | 11/2005 | Waters | 362/373 |

FOREIGN PATENT DOCUMENTS

| | | |
|---|---|---|
| DE | 295 11 927 U1 | 2/1997 |
| DE | 100 10 638 A1 | 3/2000 |

| | | | |
|---|---|---|---|
| EP | 0 116 405 A1 | 8/1984 |
| EP | 0 191 500 | 8/1986 |
| EP | 0 266 038 B1 | 10/1991 |
| EP | 0 320 080 B1 | 8/1993 |
| EP | 0 672 435 A1 | 9/1995 |
| EP | 0 678 282 A2 | 10/1995 |
| EP | 709 698 | 5/1996 |
| EP | 0 755 662 A1 | 1/1997 |
| EP | 0 780 103 A2 | 6/1997 |
| EP | 0 879 582 A2 | 11/1998 |
| EP | 0568666 B1 | 11/1999 |
| GB | 2 212 010 A | 7/1989 |
| GB | 2 218 636 A | 11/1989 |
| GB | 2 329 756 A | 3/1999 |
| JP | 51-42607 | 4/1976 |
| JP | 58-033859 | 2/1983 |
| JP | 61-158980 | 8/1986 |
| JP | 62-0066957 | 3/1987 |
| JP | 63-271983 | 11/1988 |
| JP | 04-066957 | 3/1992 |
| JP | 06-030275 A | 2/1994 |
| JP | 6285508 A | 10/1994 |
| JP | 7163863 A | 6/1995 |
| JP | 07-240536 | 9/1995 |
| JP | 8-116093 | 5/1996 |
| JP | 08-116093 | 5/1996 |
| JP | 8141001 A | 6/1996 |
| JP | 09-010238 | 1/1997 |
| JP | 8194786 A | 7/1997 |
| JP | 10-033573 A | 2/1998 |
| WO | WO 83/01311 A1 | 4/1983 |
| WO | WO 84/04463 A1 | 11/1984 |
| WO | WO 92/02275 A1 | 2/1992 |
| WO | WO 93/09847 A1 | 5/1993 |
| WO | WO 93/21842 A1 | 11/1993 |
| WO | WO 95/07731 A1 | 3/1995 |
| WO | WO 95/19810 A1 | 7/1995 |
| WO | WO 95/26217 A1 | 10/1995 |
| WO | WO 97/36552 A1 | 10/1997 |
| WO | WO 97/37722 A1 | 10/1997 |
| WO | WO 97/46279 A1 | 12/1997 |
| WO | WO 97/46280 A1 | 12/1997 |
| WO | WO 98/03131 A1 | 1/1998 |
| WO | WO 98/04317 A1 | 2/1998 |
| WO | WO 99/09071 A1 | 2/1999 |
| WO | WO 99/11324 A1 | 3/1999 |
| WO | WO 99/20346 A1 | 4/1999 |
| WO | WO 99/35995 A1 | 7/1999 |
| WO | WO 00/01464 A2 | 1/2000 |
| WO | WO 00/02491 A1 | 1/2000 |
| WO | WO 00/13608 A1 | 3/2000 |
| WO | WO 00/15296 A1 | 3/2000 |
| WO | WO 01/14012 A1 | 3/2001 |

OTHER PUBLICATIONS

LumiLeds Lighting LLC, *Application Breif AB20-5, replaces AN1149-5, Secondary Optics Design Considerations for Super Flux LEDs*, Copyright © 2002 LumiLeds Lighting, Publication No. AB20-5.

Burgess, John et al., *An Evaluation of Four Light-curing Units Comparing Soft and Hard Curing*, Pract. Periodont. Aesthet. Dent. 11(1), 125-132, 1999.

Feltzer, A.J. et al., *Influence of Light Intensity on Polymerization Shrinkage and Integrity of Restoration-cavity Interface*, Eur. J. Oral Sciences, 103, 322-326, 1995.

Kanca, III, John et al., *Pulse Activation:Reducing Resin-Based Composite Contraction Stresses at the Enamel Cavosurface Margins*, Am. J. of Dentistry, 12(3), 107-112, 1999.

Kato, Hiromasa, *Relationship Between the Velocity of Polymerization and Adaption to Dentin Cavity Wall of Light-Cured Composite*, Dental Materials J. 6(1), 32-37, 1987.

Koran, Peter et al., *Effect of Sequential Versus Continuous Irradiation of a Light-Cured Resin Composite on Shrinkage, Viscosity, Adhesion, and Degree of Polymerization*, Am. J. of Dentistry, 11, No. 1, 17-22, 1998.

Mayes, Joe H., *Curing Lights: An Overview*, Ormco, vol. 9, No. 2, 2000, p. 15-17.

LumiLeds Lighting LLC, *Lumen Maintenance of White Luxeon™ Power Light Sources*, Application Brief AB07, LumiLeds Lighting, US LLC, 2006.

LumiLeds Lighting LLC, *Application Breif AB20-5, replaces AN1149-5, Secondary Optics Design Considerations for Super Flux LEDs*, Copyright © 2002 LumiLeds Lighting, Publication No. AB20-5.

Burgess, John et al., *An Evaluation of Four Light-curing Units Comparing Soft and Hard Curing*, Pract. Periodont. Aesthet. Dent. 11(1), 125-132, 1999.

Feltzer, A.J. et al., *Influence of Light Intensity on Polymerization Shrinkage and Integrity of Restoration-cavity Interface*, Eur. J. Oral Sciences, 103, 322-326, 1995.

Kanca, III, John et al., *Pulse Activation:Reducinq Resin-Based Composite Contraction Stresses at the Enamel Cavosurface Margins*, Am. J. of Dentistry, 12(3), 107-112, 1999.

Kato, Hiromasa, *Relationship Between the Velocity of Polymerization and Adaption to Dentin Cavity Wall of Light-Cured Composite*, Dental Materials J. 6(1), 32-37, 1987.

Koran, Peter et al., *Effect of Sequential Versus Continuous Irradiation of a Light-Cured Resin Composite on Shrinkage, Viscosity, Adhesion, and Degree of Polymerization*, Am. J. of Dentistry, 11, No. 1, 17-22, 1998.

Mayes, Joe H., *Curing Lights: An Overview*, Ormco, vol. 9, No. 2, 2000, p. 15-17.

Mehl, A. et al., *Physical Properties and Gap Formation of Light-Cured Composites With and Without 'Softstart-Polymerization'*, J of Dentistry, 25, 321-330, 1997.

Sakaguchi, Ronald L. et al., *Recuded Light Energy Density Decreases Post-Gel Contraction While Maintaining Degree of Conversion in Composites*, J. of Dentistry, 26, 695-700, 1998.

Schlager, Kenneth J., et al., *An LED-Array Light Source for Medical Therapy*, SPIE vol. 1892, Medical Lasers and Systems II, p. 26-35, 1993.

Swift Jr., Edward et al., *Contemporary Photocuring Issues, Part II*, J. Esthetic Dentistry, 12(1), 50-57 2000.

Tarle, Z. et al., *The Effect of the Photopolymerization Method on the Quality of Composite Resin Samples*, J. of Oral Rehab, 25, 436-442, 1998.

\* cited by examiner

OPTICAL IRRADIATION DEVICE HAVING LED AND HEAT PIPE

TECHNICAL FIELD

This invention relates to an optical irradiation device, especially a compact portable irradiation device suitable for use as a light polymerisation source.

It has already been proposed to use light-emitting diodes LEDs in a hand held device to produce a focused beam of light to cure dental materials. Blue light at a peak wavelength of about 470 nm is used to harden dental polymers which contain camphoroquinone as the photoinitator in a methacrylate polymerisation process. However, there is a problem in producing a sufficient level of irradiance even with a clustered array of LEDs, to cure the known dental polymers in the recommended time. At the lower levels of irradiance available generally below 300 mW/sq.cm, longer curing times have to be allowed, which reduces the efficiency of the dental treatment delivered.

DISCLOSURE OF THE INVENTION

An object of the present invention is to provide an optical irradiation device that employs LEDs, and thereby has the benefits of compactness, portability, ruggedness and long life, but which also produces improved levels of irradiance at and above 300 mW/sq.cm.

According to a first aspect of the invention, LEDs are clustered in an irradiation device by forming shaped facets on adjacent LEDs which allow them to adjoin more closely than they would otherwise with conventional spherical outer surfaces as manufactured currently.

According to a second aspect, the invention consists in a tapered light guide for an optical irradiation device, which light guide is tapered from its input end to its output end and has an intermediate region of minimum diameter in which a bend is formed.

According to a third aspect, the invention consists in an optical irradiation device employing LEDs and incorporating a heat pipe to cool the LEDs.

According to a fourth aspect, the invention consists in a heat pipe comprising inner and outer walls that extend longitudinally from one end of the heat pipe to the other and define an annular space therebetween containing a material that serves to absorb heat by a phase change, the annular space being divided by internal walls into a plurality of fluid flow channels that extend longitudinally between said ends, some of said channels being adapted to conduct the liquid/vapour phase of said material from the hot end of the heat pipe to the cold end, and other channels being adapted to return said liquid phase from the cold end of the pipe to the hot end.

According to a fifth aspect, the invention consists in an irradiation device employing LEDs and a tapered light guide to collect radiation emitted by the LEDs and deliver this to an output beam, wherein two or more tapered light guides are arranged in series so that successive guides receive radiation from preceding guides, and a group of LEDs is provided at the input end of each guide, each successive guide preferably being provided with a ring of LEDs around the output end of the preceding guide.

The first aspect of the invention means that LEDs occupy more of the available space, and a fixed number produce a higher radiant intensity. Thus, smaller numbers of LEDs can be used to produce a desired level of irradiance, which in turn reduces the power required to drive the device and the heat generated by it. Furthermore, the device can be made more compact. Packing of the LEDs in this way may involve a slight reduction in the output of each LED, but the more effective packing density produces an overall increase in irradiance.

Typically, a central LED might have a polygonal outer surface, and a first ring of LEDs would be arranged around it, each with a flat face to abut a corresponding face of the central LED and possibly each having a pair of radiating side faces which abut adjacent LEDs in the first ring. Furthermore, a second or more rings of LEDs could be arranged concentrically with the first ring, each with respective adjacent flat side faces abutting one another and possibly with inwardly diverted faces abutting respective outwardly directed faces of the LEDs of the inner ring. Alternatively, a single ring or two or more concentric rings of LEDs could be used without a central LED.

DESCRIPTION OF THE DRAWINGS

The invention will now be described by way of example with reference to the accompanying drawings, in which.

MODE OF CARRYING OUT THE INVENTION

In a typical optical irradiation device according to the invention, a plurality of LEDs are clustered together so as to direct emitted radiation into a single beam. A cluster of LEDs 43 is shown in side view in FIG. 4, and in plan view or cross-section in FIGS. 1 to 3. Each LED comprises a light-emitting semiconductor Pn junction (not shown) which is encapsulated in an outer plastics envelope, the profile of which is shown in the drawings. The sides of the LED envelope are shaped to allow the LEDs to be clustered together more closely at their bases, thereby increasing the ratio of occupied to unoccupied space in the cluster of LEDs. The tips of the LEDs are substantially spherical and transmit the radiation to form the beam.

Figures 1, 2:
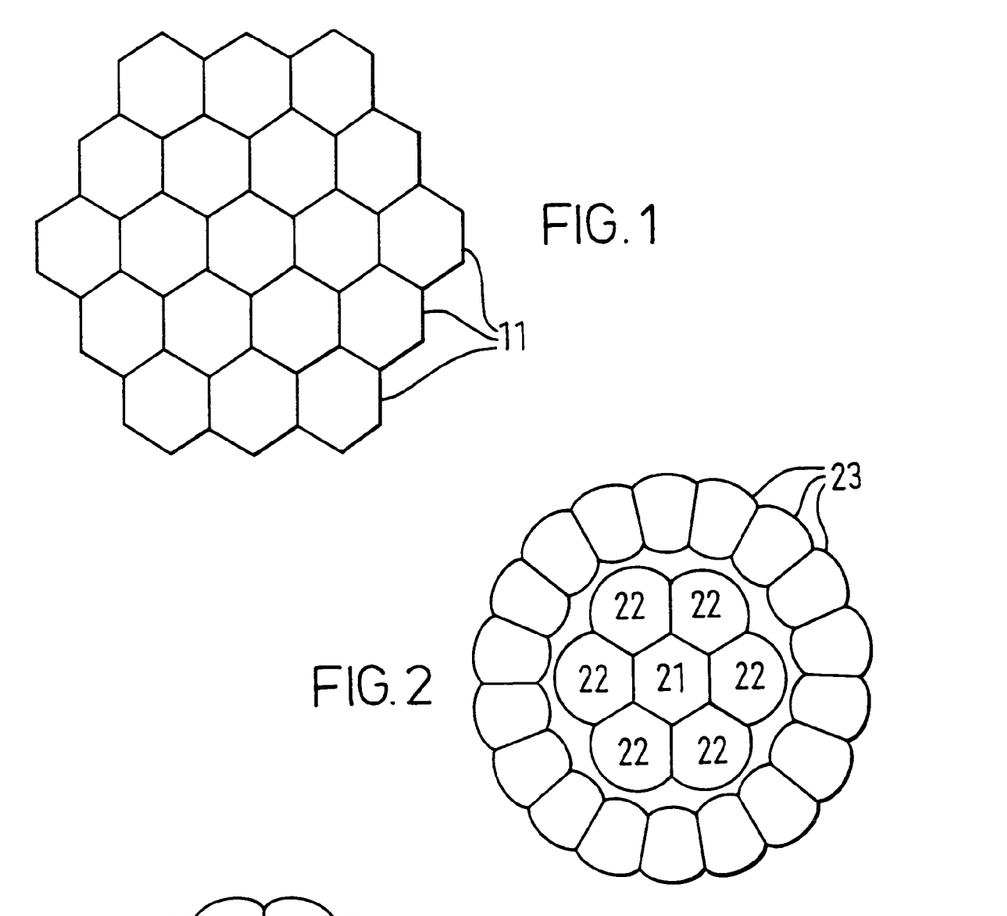
FIG. 1 is a schematic cross-section through a first embodiment of the invention comprising a cluster of hexagonal section LEDS.
FIG. 2 is a schematic cross-section through a second embodiment of the invention comprising a cluster of an inner group of LEDS and an outer ring of LEDS.

In the embodiment of the invention illustrated in FIG. 1 the outer envelope of the LEDs is hexagonal in cross-section, and the LEDs are clustered in the manner of a honeycomb as shown, with adjacent facets abutting one another.

In the second embodiment of the invention illustrated in FIG. 2, a central LED 21 of hexagonal cross-section has facets which abut adjacent facets of six LEDs 22 in a first ring of LEDs with radially extending side facets that allow adjacent LEDs in the ring to abut one another. A second ring of LEDs 23 is arranged around the first ring of LEDs, and these LEDs 23 have radially extending side facets that allow adjacent LEDs in the ring to abut one another.

Figure 3:
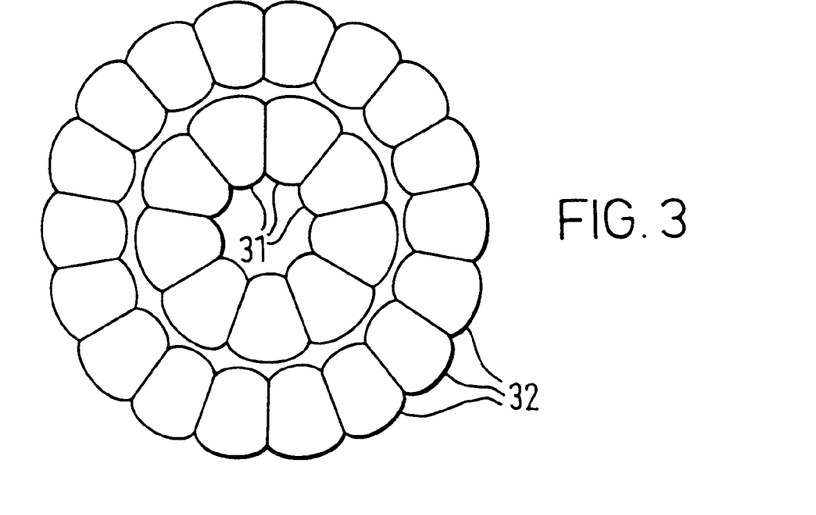
FIG. 3 is a schematic cross-section through a third embodiment of the invention comprising a cluster of two rings of LEDS.

In a third embodiment of the invention shown in FIG. 3, an inner ring of nine LEDs 31 in a first ring is contained within a second ring of LEDs 32, and radially extending side facets of the LEDs in both rings allow adjacent LEDs in each ring to abut one another.

Both the second embodiment of FIG. 2 and the third embodiment of FIG. 3 may be modified by the addition of one or more further concentric rings of LEDs. Also, the circumferential facets of the LEDs of each ring may be shaped to abut similarly shaped circumferential facets of the adjacent ring of LEDs.

In yet another embodiment, the central group of LEDs 21,22 of FIG. 2 may be replaced by the same number of LEDs in a honeycomb cluster. Yet another embodiment may consist of the single ring of LEDs 31 shown in FIG. 3. It will be appreciated in all three illustrated embodiments, the LEDs are mounted in a substantially flat plane.

In modifying the conventional optical sphere shape of the outer plastics envelope of a LED care has to be taken to preserve as much as possible of the focusing effect of the envelope to maximise the total irradiance. However, because the envelope of existing LEDs have a tapered shape to assist their removal from the mould during manufacture, the shaped side facets can be formed around the broader base of the LED to change its cross-section, for example to become hexagonal, but with these facets having a reducing effect on the shape of the envelope towards its tip where the focusing effect of the envelope is concentrated. Thus the invention can employ existing LEDs and modify their shape in a secondary manufacturing process, for example, using jigs, or the invention can employ LEDs which have been specially manufactured with the required outer envelope shape to accommodate better clustering.

The shaped facets of the LEDs may be polished to enhance reflection and help reduce any loss of optical powers. Additionally, a reflective metallic film may be applied to the shaped facets to further enhance reflection.

The LEDs may also incorporate a microlens or microlens array to aid collimation of the beam.

The electrical connections of the LEDs, known as lead frames 44, are connected to respective positive and negative power terminals or bus bars 42. Preferably, these terminals are adapted to serve the dual function of heat sinks to help remove heat generated by the LEDs 43. Thus, the terminals are formed of a good thermal conductor such as copper, and are located in the optimum location relative to the LEDs and the external surfaces of the device. In one particular embodiment most suited to the LED array of FIG. 3, the terminals 42 take the form of two concentric rings, each lying adjacent to the bases of one ring of LEDs 31 or 32. Preferably, the negative terminal is the outer one because the lead frames 44 to the negative terminal of the LEDs generally get hotter than the lead frames 44 to the positive terminal of the LEDs.

Figure 4:
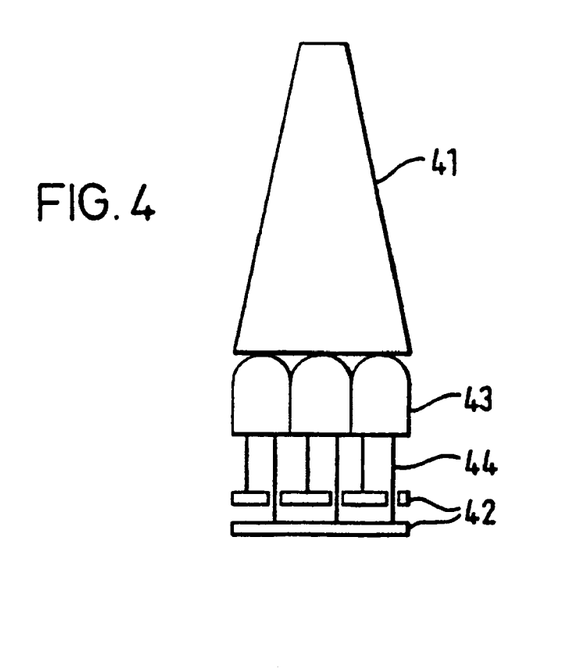
FIG. 4 is a schematic side elevation of a fourth embodiment of the invention.

The typical optical irradiation device according to the invention also preferably incorporates a tapered light guide, shown as guide 41 in FIG. 4, to collect light emitted by the LEDs and deliver this as an output beam. It is known to use light guides with adiabatic optical tapers in optical irradiation devices so that there is total internal reflection of the light as it is conducted from the light source to the output. However, an advantage of the invention is that the more compact cross-section of the LED cluster means that the diameter at the input end of the light guide can be smaller, and thus a smaller angle of adiabatic taper (i.e. the ratio of the diameter of the input end to the output end of the light guide) can be provided in the light guide with the consequent more efficient transmission of radiant energy and increased illuminance. This improvement is most marked compared with a conventional approach of simply increasing the numbers of LEDs in a cluster at ever increasing diameters with decreasing beneficial effect on illuminance and increasing detrimental effect on compactness, heat generation and cost. In another embodiment of the invention, illustrated in FIG. 6, two or more adiabatic tapered light guides 41' are arranged in series, each with a corresponding cluster of LEDs 43", 43''', but with successive clusters forming a ring around the end of one light guide as it connects to the next. Alternatively, each successive ring of LEDs 43''' may be replaced by just one or a fewer number of LEDs. This arrangement allows the overall diameter of the device to be kept relatively small as the LED clusters 43", 43''' are arranged in groups along the length of the device.

Figure 5:
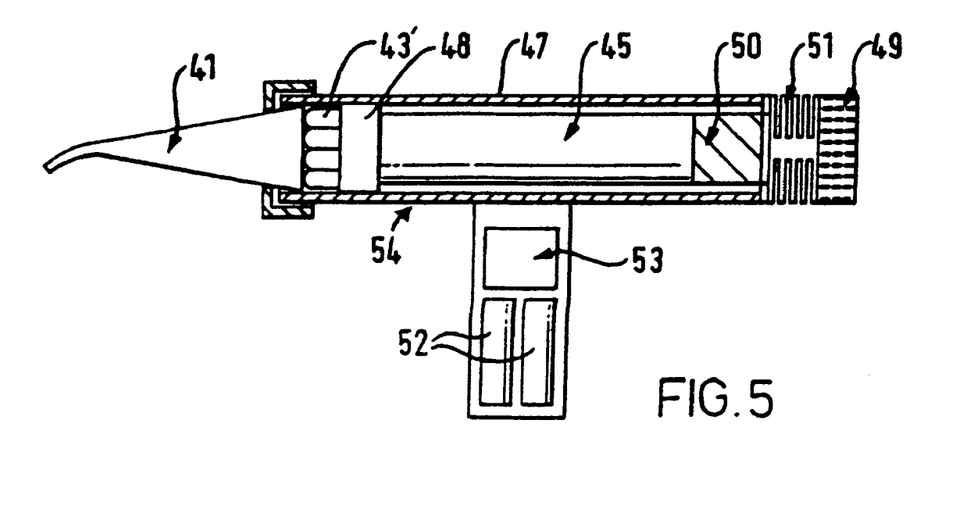
FIG. 5 is a schematic longitudinal section through a fifth embodiment of the invention.

In the preferred embodiment of FIG. 4, a single tapered light guide 41 is provided. If required, the light guide can be curved along its length, as shown in FIG. 5, to direct the output beam to suit a particular application, this being a known practice with existing light guides. The light guide may be machined from cast acrylic plastic and bent, or could be made from glass or other optically transparent materials.

Figure 8:
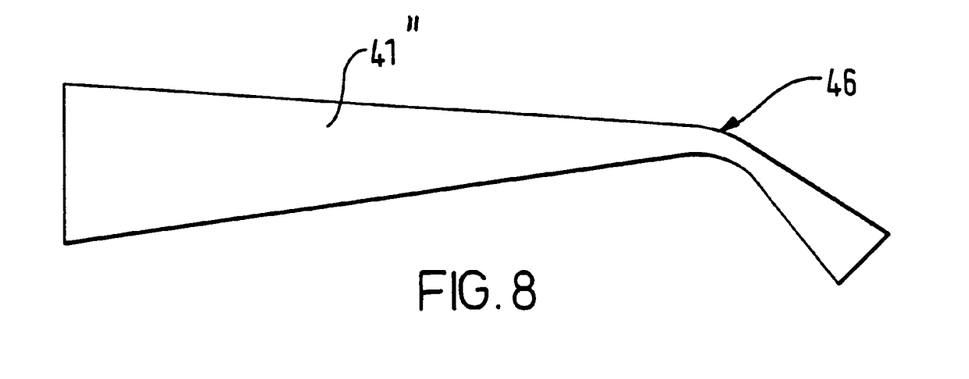
FIG. 8 is a schematic side elevation of a tapered light-guide according to another embodiment of the invention.

An alternative light guide is illustrated in FIG. 8 in which the bend in the light guide 41 is provided at a waisted section 46 in its length which reduces to a minimum diameter before widening again to a larger diameter towards its output end. By forming the bend at the minimum diameter, the light transmission losses of the light guide caused by the bend are reduced, but the effective cross-sectional area of the output beam is maintained at the required level.

Fused fibre-bundle light guides have the advantage of individual fibres being of a relatively small diameter so that they can be bent over a tighter radius without the greater losses associated with larger diameter fibres when bent over the same radius. However, conventional fused-fibre bundles have the disadvantage of a packing fraction loss, that is, the outer cladding of the fibre uses up a significant proportion of the cross-section of the light guide into which light from the semiconductor array is directed, thus reducing the amount of transmitted radiation available from the semiconductor source. Preferably, therefore, in one embodiment of the invention, illustrated in FIG. 7, the guide comprises a few shaped fibres 61, 61' placed adjacent to each other and fused together.

Figure 7:
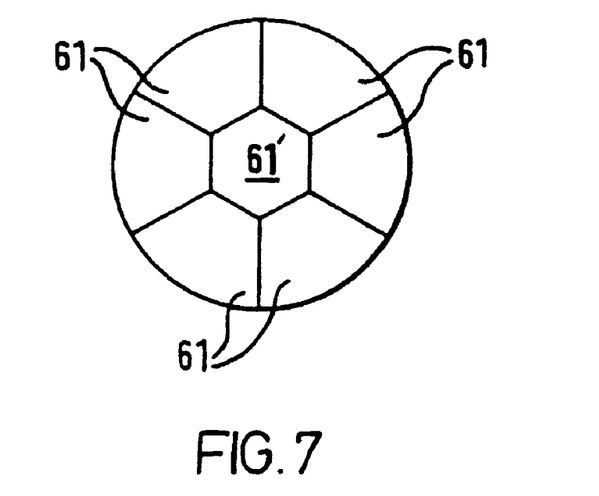
FIG. 7 is a schematic cross-section through a bundle of light guide fibres with modified sections.

A guide of this design is manufactured by MicroQuartz Sciences Inc. of Phoenix, Ariz., USA. In this way, the diameter of each fibre is smaller than a single homogeneous guide rod so that they allow greater light transmission on bending around the same bend radius, but also the packing fraction is also greatly reduced over conventional fibre guides, resulting in a greater than 90% core availability at the input end of the guide.

In another embodiment of the invention, a graded-index optical light guide is used. A graded-index light guide has no sudden interface between the cladding and the core. Instead, the refractive index varies either radially or axially. In one embodiment, the gradient of the refractive index of the light guide varies both radially and axially so that the light energy is favourably manipulated. A guide that uses a stepped index could also be used with the same axial and radial variation in refractive index. In this way, the numeric aperture can be varied at either end of the guide to achieve the desired transmission.

In other embodiments of the invention, instead of providing a single tapered light guide, each LED or groups of LEDs could be provided with its own light guide fibre incorporating an adiabatic optical taper, and the output ends of these fibres could be collected together to form a single output beam. The input end of the fibre would be moulded optically to the adjacent LED or group of LEDs for efficient transmission of radiation. In this way, the diodes can be spaced more widely to dissipate unwanted heat. In yet another embodiment of the invention, each LED could be adjusted so that its outer envelope is extended into a fibre light guide which incorporates an adiabatic optical taper. In yet another embodiment, the section of the fibres may be modified so that shaped faces of the fibres fit together to reduce the interstitial space. One embodiment of this design could be as shown in FIG. 7.

The light guide or light guides used according to the invention may be formed with an outer metallic coating to improve its performance.

It will be appreciated that the irradiance of the device according to the invention can be varied by varying the input power, number of LEDs, or by varying the adiabatic taper of the light guide.

Cooling of the LED cluster can be aided according to another feature of the invention by arranging that the electrical connections of each LED are thermally connected to one or more heat pipes. Conventional LED irradiation devices usually include a heat sink to conduct away the heat from the LED chips. Heat sinks are generally slow and inefficient in conducting heat away from a heat source compared with heat pipes. Heat pipes conduct heat away rapidly by using the latent heat of a substance, such as water, which is vaporised by the heat from the source. The vapour moves at high speed to the cooler end of the heat pipe and condenses. Heat pipes are unique in their ability to conduct heat rapidly in this way.

FIG. 5 shows a device according to the invention which incorporates a light guide 41 and cluster of LEDs 43 as shown in FIG. 4 together with a heat pipe 45 as a single lumen in the main body 54 of the device. The hotter of the LED leads is preferably placed nearer the heat pipe 45 or outer case 47 of the LED cluster so that the heat path of the hotter lead is shorter. A thermal connector 48 may be provided between the LEDs 43' and the end of the heat pipe 45.

If required, additional forced cooling means may be used for example, a fan 49 or Peltier device 50 in juxtaposition to the pipe. In addition, a heat sink 51 may be provided.

Because of the greater cooling ability of heat pipes, they allow the LEDs to be driven in such a manner as to produce more radiation, and thus allows a more powerful device to be manufactured.

Figure 9:
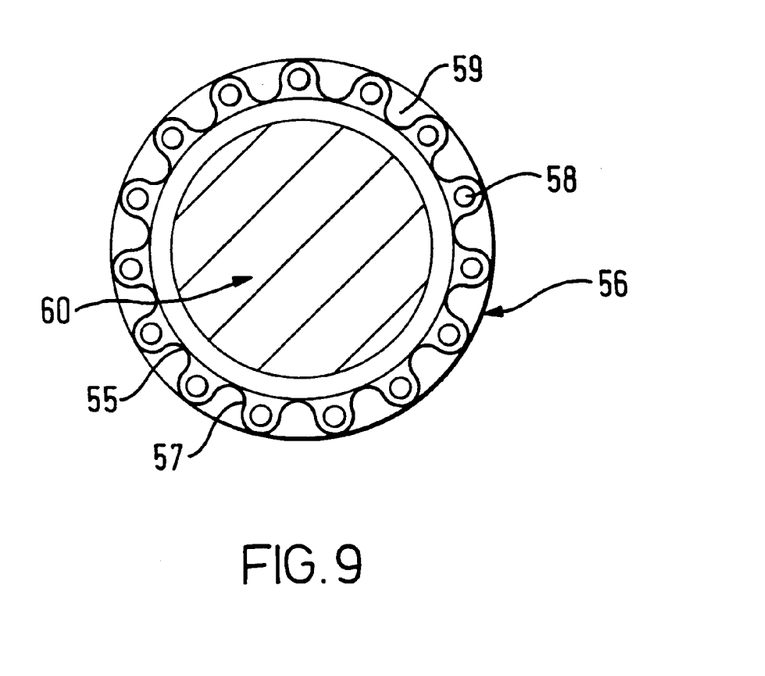
FIG. 9 is a schematic cross-section through a heat pipe according to the invention.

For portable use, the LEDs are operated from batteries 52, which are located in a hand grip 53 attached to the body 54, in FIG. 5. However, the heat pipe design can be modified as shown in FIG. 9 to accommodate batteries. The heat pipe consists of two concentric heat conducting tubes 55,56 with a folded interstitial heat conduction element 57 between these tubes similar in appearance to a length of corrugated sheet rolled into a tube. This lies within the concentric tubes. The wicks 58 of the heat pipe can then be placed in alternative grooves in the corrugated sheet, while the empty grooves 59 allow for the rapid movement of the vapour formed at the warmer end of the heat pipe.

By designing the heat pipe in this way batteries, capacitors, supercapacitors or other energy source 60 can be located within the inner tube 55 of the heat pipe.

In some embodiments, for example, where there are a large number of LEDs, a heat sink 51 may be necessary in addition to the heat pipe 45. The intermittent use of an LED irradiation device for dental curing, means that with careful design, a heat sink may be omitted. If cooling to below the ambient temperature is required, such as may be the case in extreme environments, a Peltier device 50 may be added to the heat pipe, although a Peltier device will result in a greater consumption of power and a requirement for greater heat dissipation.

The wavelengths of the LED used will depend upon the applications of the device. A LED emitting blue light with a peak wavelength of about 470 mm is used to harden dental polymers, but a LED emitting red light may be useful for photodynamic therapy, for example, cancer therapy.

The wavelength of light emitted by the LEDs may be modified in a light guide by doping the material from which it is composed with fluorescent material. This can serve to lengthen the wavelength of the emitted light so as to suit the particular application.

The choice of LED is also important in terms of its construction, diameter, irradiance and light angular spread pattern, From a range of known LEDs the best available choice has been determined as that with a 3 mm diameter rather than a 5 mm diameter and an angular spread of 30 degrees rather than 15 or 45 degrees. Nichia is the manufacturer of these LEDs.

It will be appreciated that the term "light-emitting diode-LED" as used herein also includes laser diodes.

Figure 6:
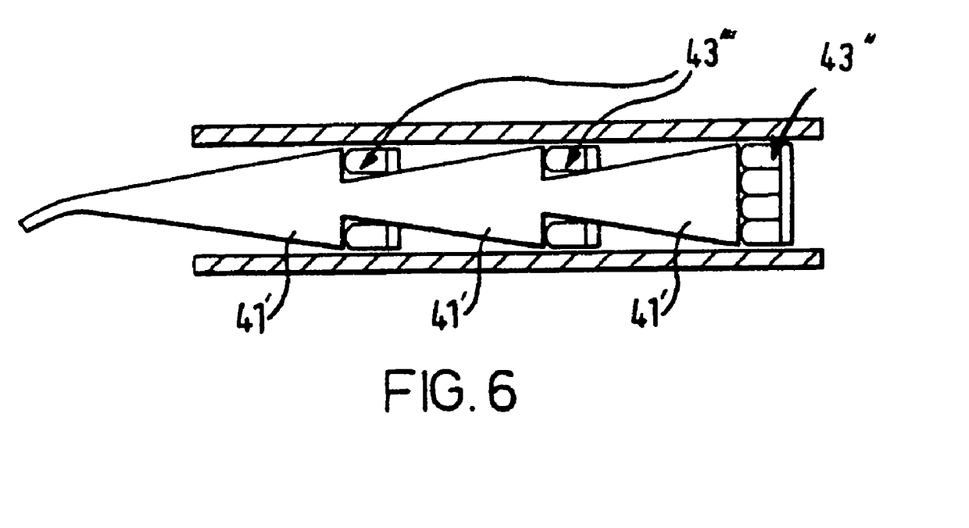
FIG. 6 is a schematic longitudinal section through a sixth embodiment of the invention.

LEDs in the devices according to the invention may be operated in a pulsed mode or modulated mode to vary the output radiation intensity to suit the application, and multiple clusters of LEDs, such as in the embodiment of FIG. 6, may each be generated in a different mode.

The power supply for the LEDs of the device according to the invention could be mains power, battery power, capacitor, supercapacitor, solar power, clockwork generator or generator powered by the mechanical effort of the operator or assistant.

In one embodiment, a capacitor or supercapacitor could be used to power the array having advantages over conventional rechargeable sources such as batteries. Capacitors can be virtually instantaneously recharged between one or more curing cycles of operation when the unit is connected to a power source.

The power supply for the device may be re-chargeable, and may be designed to make automatic electrical contact with the charging means of a base unit when engaged with the latter in the manner of a cordless telephone handset.

The invention claimed is:

1. An optical irradiation device comprising a radiation source including a plurality of LEDs thermally connected to a heat pipe and disposed at an end thereof, a unitary thermal connector directly connecting the plurality of LEDs and the heat pipe for conducting heat away from the plurality of LEDs and a power supply configured to provide power to the plurality of LEDs, wherein the heat pipe includes an outer element, and an inner element having an inner wall configured to accommodate at least a portion of the power supply therewithin.

2. The optical irradiation device according to claim 1 further comprising a heat sink in thermal contact with the heat pipe.

3. The optical irradiation device according to claim 1, wherein the heat pipe provides a means for cooling the plurality of LEDs such that the plurality of LEDs are capable of being driven to produce more radiation than the plurality of LEDs would be capable of without the heat pipe.

4. The optical irradiation device according to claim 1, wherein the plurality of LEDs are formed into one or more clusters.

5. The optical irradiation device according to claim 1, wherein the plurality of LEDs are formed into one or more arrays.

6. The optical irradiation device according to claim 1, wherein the optical irradiation device is sized and configured as a hand-held device.

7. The optical irradiation device according to claim 1 further comprising a fan or Peltier device proximate to the heat pipe.

8. The optical irradiation device according to claim 7, further comprising a heat sink in thermal contact with the heat pipe.

9. The optical irradiation device according to claim 1, wherein the power supply includes a stored energy device, and wherein at least a portion of the stored energy device is located within the inner wall.

10. The optical irradiation device according to claim 9, wherein the power supply includes any of a battery, a capacitor and a supercapacitor located within the inner wall.

11. The optical irradiation device according to claim 1, wherein the outer element and the inner element are tubular in shape and the outer element is located concentrically about the inner element.

12. The optical irradiation device according to claim 11, wherein the heat pipe includes a substance capable of a phase change as a result of heat absorption, and wherein the substance is located between the inner element and the outer element.

13. The optical irradiation device according to claim 11, wherein the heat pipe includes at least one wick located between the inner element and the outer element.

14. The optical irradiation device according to claim 11, wherein the heat pipe includes a folded heat conduction element located concentrically about the inner element radially inward of the outer element.

15. The optical irradiation device according to claim 14, wherein the folded heat conduction element in combination with the inner element and the outer element provides a plurality of channels.

16. The optical irradiation device according to claim 15, wherein a plurality of wicks are located in alternate channels, respectively, included in the plurality of channels.

* * * * *